(12) United States Patent
Francis

(10) Patent No.: US 8,531,673 B2
(45) Date of Patent: Sep. 10, 2013

(54) APPARATUS FOR ABSOLUTE VARIABLE ANGLE SPECULAR REFLECTANCE MEASUREMENTS

(75) Inventor: Robert John Francis, Glenn Waverley (AU)

(73) Assignee: Agilent Technologies Australia (M) Pty Ltd, Victoria (AU)

( * ) Notice: Subject to any disclaimer, the term of this patent is extended or adjusted under 35 U.S.C. 154(b) by 27 days.

(21) Appl. No.: 13/165,376

(22) Filed: Jun. 21, 2011

(65) Prior Publication Data

US 2012/0019808 A1 Jan. 26, 2012

(30) Foreign Application Priority Data

Jul. 21, 2010 (AU) ................................ 2010903271

(51) Int. Cl.
*G01N 21/47* (2006.01)
(52) U.S. Cl.
USPC .......................................... 356/446; 356/445

(58) Field of Classification Search
USPC ................... 356/237.2–237.6, 440, 442–448; 702/1, 33, 35, 40
See application file for complete search history.

(56) References Cited

U.S. PATENT DOCUMENTS

| | | | |
|---|---|---|---|
| 2004/0207836 A1* | 10/2004 | Chhibber et al. | 356/237.4 |
| 2010/0004875 A1* | 1/2010 | Urano et al. | 702/40 |
| 2010/0007863 A1* | 1/2010 | Jordanoska | 355/53 |

* cited by examiner

Primary Examiner — Tri T Ton

(57) ABSTRACT

An apparatus for measuring specular reflectance of a sample is provided including a light source for transmitting a beam of light at an angle of incidence onto a surface of a sample; a polarizing filter comprising a wire grid that avoids a need for collimation of the incident beam of light; a sample holder for mounting the sample; and a detector assembly for detecting a beam of light which is specularly reflected from a surface of the sample; wherein the sample holder and detector assembly are mounted for relative movement, such that the light source, the detector assembly and the sample holder are relatively positionable for a specularly reflected component of a transmitted light beam to be detected for different angles of incidence of the light beam.

16 Claims, 1 Drawing Sheet

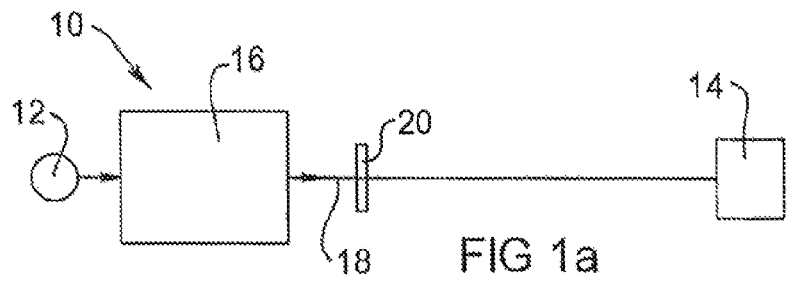
FIG 1a
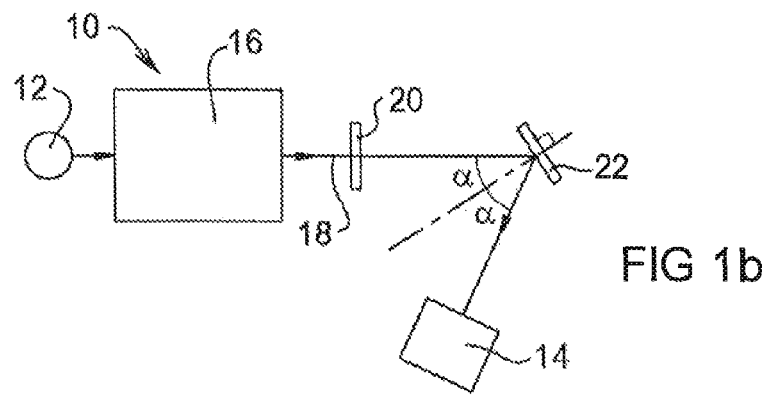
FIG 1b
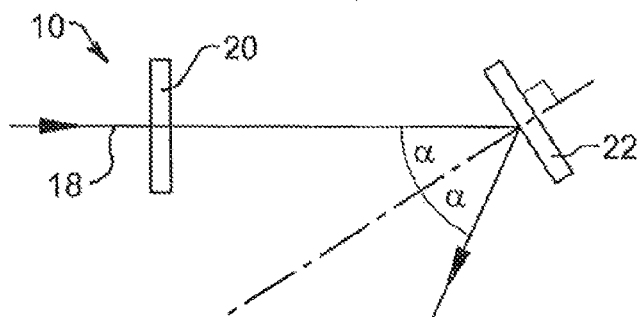
FIG 2
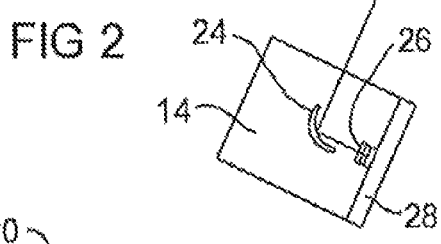
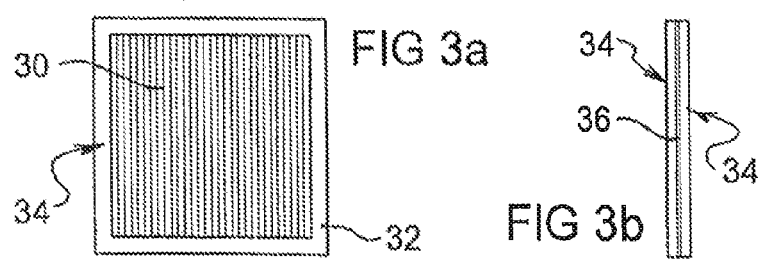
FIG 3a FIG 3b

APPARATUS FOR ABSOLUTE VARIABLE ANGLE SPECULAR REFLECTANCE MEASUREMENTS

FIELD OF THE INVENTION

The present invention relates to apparatus for measuring specular reflectance of a sample and an accessory for use in a spectrometer for measuring specular reflectance of a sample.

BACKGROUND TO THE INVENTION

The accurate measurement of specular reflectance over a range of wavelengths from ultra violet through near infrared and over a range of angles of incidence, is a prerequisite to the design and manufacture of a variety of modern optical components.

In spectrometers the light source and the light detector are usually fixed in position. The specular reflectance apparatus diverts the light beam onto a sample of interest and re-orients the reflected light onto the detector. This involves use of a number of mirrors that redirect and refocus the light beam to allow for changes in the length of the path between the light source and the detector. The mirrors are usually fixed and/or movable in position. The need for a plurality of mirrors makes such apparatus complex. Moreover the mirrors tend to deteriorate with handling and exposure to the atmosphere, progressively degrading the overall performance of the apparatus.

Measuring absolute specular reflectance as a function of the angle of incidence of the light beam avoids the need for multiple mirrors but requires considerably more complex optical arrangements than conventional spectrometers. The principle requires two measurements to be made, that is a first reference measurement excluding the sample and a second measurement that determines the reflectance of the sample.

One suitable arrangement involves switching between the reference and sample measurement configuration by rotating a mirror and translating the detector assembly automatically. The mirror rotates to direct the light beam onto the sample whose specular reflectance is to be measured. At the same time, the detector assembly is translated so as to maintain the same relationship with the input beam derived from the light source. The total length of the optical path remains the same so that the ratio of the two measurements provides the reflectance of the sample. A new reference measurement is required for each new angle of incidence as well as each different angle of polarisation.

Detectors having uniform sensitivity across their surface are required in such apparatus. Detectors not having uniform sensitivity require compensatory measures such as use of a scrambling light pipe to reduce sensitivity of the apparatus to misalignment of the beam of light. Moreover, most detectors are limited to a particular range of wavelengths of light. As a result, in order to cover a broad range of wavelengths it is necessary to employ multiple detectors, each detector catering for a portion of the desired wavelength range. This substantially increases the complexity of the apparatus since means for switching between the detectors must be provided in the form of a mechanical movement of each detector, or a mechanical movement of an optical component to shift the beam of light. These types of mechanisms invariably add bulk and complexity to the apparatus.

Other arrangements involve an integrating sphere to scramble the beam of light and reduce sensitivity to misalignment of the beam of light and/or non uniform sensitivity of the detector employed. An integrating sphere can accommodate multiple detectors and does not require mechanical changes between wavelength ranges. However, the application of integrating spheres is limited to restricted wavelength ranges and significantly reduces signal levels.

Other issues with apparatus for measuring absolute specular reflectance include that every specular reflectance at least partially polarises the reflected beam. The amount of polarisation is dependent on the nature of the sample and the angle of incidence. Accordingly, in order to accurately measure the spectral reflectance of a sample, it is necessary to measure both the intensity and the polarisation of the reflected light.

Accordingly, it is recognised that the range of commercial spectrometer apparatus and accessories currently available have various limitations.

The discussion of the background to the invention herein-above is included to explain the context of the invention. This is not to be taken as an admission that any of the material referred to was published, known or part of the common general knowledge in Australia as at the priority date of the present application.

An object of the present invention is to provide relatively simple spectrometer apparatus and accessory providing improved accuracy and efficiency by addressing at least one of the aforementioned limitations.

SUMMARY OF THE INVENTION

According to a first aspect of the present invention, there is provided an apparatus for measuring specular reflectance of a sample including:

a light source for transmitting a beam of light at an angle of incidence onto a surface of a sample;

a polarising filter comprising a wire grid which avoids a need for collimation of the incident beam of light;

a sample holder for mounting the sample; and a detector for detecting the beam of light which is specularly reflected from the surface of the sample;

wherein the sample holder and detector are mounted for relative movement, such that the light source, the detector and the sample holder are relatively positionable for a specularly reflected component of a transmitted light beam to be detected for different angles of incidence of the light beam.

According to a second aspect, the present invention is realisable as an accessory for use in a spectrometer wherein the light source is a component of the spectrometer and not the accessory. Thus the present invention provides an accessory apparatus for a spectrometer for measuring specular reflectance of a sample including:

a polarising filter comprising a wire grid so as to avoid a need for collimation of an incident beam of light emitted by a light source;

a sample holder for mounting the sample wherein the beam of light is transmitted onto a surface of the sample at an angle of incidence; and a detector for detecting the beam of light which is specularly reflected from a surface of the sample;

wherein the sample holder and detector are mounted for relative movement, such that the light source, the detector and the sample holder are relatively positionable for a specularly reflected component of a transmitted light beam to be detected for different angles of incidence of the light beam.

Preferably, the polarising filter comprises a pair of polariser plates, each polariser plate including a wire array, the polariser plates being mounted face to face with an air gap there between and such that the wire arrays are in parallel.

The polarising filter may provide a contrast of greater than 500 at 255 nm.

The polarising filter preferably has a thickness of 2 to 5 mm. In one particular form, the polarising filter has a thickness of 2.2 mm.

In accordance with an embodiment of the present invention, the detector assembly comprises an infra red transmitting detector and an infra red detector. The infra red detector is preferably a photovoltaic detector. The photovoltaic detector may be an indium gallium arsenide (InGaAs) detector.

In a preferred form of the invention, the detector assembly comprises a silicon detector mounted above an indium gallium arsenide (InGaAs) detector, The silicon detector may be approximately 5 mm square. The indium gallium arsenide (InGaAs) detector may be approximately 3 mm in diameter.

The accessory apparatus may further include an optical component for focussing the beam of light which is specularly reflected from the surface of the sample on the detector assembly.

In a preferred embodiment, the beam of light which is specularly reflected from the surface of the sample is focussed onto the indium gallium arsenide (InGaAs) detector.

The optical component optionally comprises a toroid mirror or an ellipsoid mirror.

In one form of the apparatus, the light source, the detector and the sample holder are correspondingly relatively positionable for a specularly reflected component of a transmitted light beam to be detected for different angles of incidence of the light beam and wherein corresponding relative positions of the light source, the sample surface and the detector are constrained such that said detector is located by said constraint to detect said specularly reflected component of said light beam at an angle of reflection, which is equal to the angle of incidence of the light beam on the sample surface, and wherein the detector for movement along an arc about said axis and the sample holder and the detector are operatively associated such that movement of the sample holder through an angle automatically rotates the detector through twice said angle.

For a better understanding of the invention and to show how the same may be performed, a preferred embodiment thereof will now be described, by way of non-limiting example only, with reference to the accompanying drawings.

BRIEF DESCRIPTION OF THE DRAWINGS

It will be convenient to hereinafter describe the invention in greater detail by reference to the accompanying figures which facilitate understanding of the method according to this invention. The particularity of the figures and the related description is not to be understood as superseding the generality of the broad identification of the invention as given in the attached claims.

FIG. 1A is a schematic showing the accessory apparatus according to an embodiment of the present invention in a reference position.

FIG. 1B is the accessory apparatus of FIG. 1A in a measurement position.

FIG. 2 is a schematic showing the accessory apparatus according to an alternative embodiment of the present invention.

FIG. 3 is a schematic showing an example polarising filter for use in accordance with an embodiment of the present invention.

DETAILED DESCRIPTION

Referring firstly to FIG. 1A, there is provided an apparatus 10 for measuring specular reflectance of a sample including a light source 12 for transmitting a beam of light onto the surface of the sample (not shown in FIG. 1A, see FIG. 2) at an angle of incidence and a detector assembly 14 for detecting the beam of light specularly reflected from the surface of the sample. The light source 12 illuminates a spectrometer 16 which disperses the beam of light and selects a limited bandwidth for presentation to the sample. The beam of light 18 transmitted through the spectrometer passes through a polariser 20. In the reference position shown in FIG. 1A, the beam of light 18 passes directly from the spectrometer 16 to the detector assembly 14 via the polarising filter 20 to provide a reference measurement.

Referring now to FIG. 1B, which shows the apparatus of FIG. 1A in the measurement position, a sample 22 is positioned at an angle "a" to the beam of light 18 transmitted through the spectrometer. The angle "a" represents the angle between the angle of incidence and the normal to a surface of the sample 22. The detector assembly 14 is positioned to collect the beam of light which is specularly reflected from the surface of the sample at an angle which equates to twice angle "a", that is angle "$2a$". The actual sample reflectance value constitutes the measurement represented by FIG. 1B divided by the reference measurement represented by FIG. 1A.

The angle "a" and "$2a$" which is set for the sample 22 and the detector assembly 14 may be set manually by selection from a set of predetermined kinematic locations on a plate. Alternatively, the relative position of the sample 22 and the detector assembly 14 can be determined using a pair of concentric computer controlled motors, or by a single motor and a pair of gears as described in International Application PCT/AU2002/00385 to the present Applicant which is hereby incorporated in its entirety by reference.

Referring now to FIG. 3, a polarising filter 20 positioned between the light source 12 and the detector assembly 14 avoids the need to measure the polarisation of the reflected beam of light. The polarising filter 20 is a custom designed polariser including an aluminium wire grid 30 mounted on a planar substrate 32, e.g. a silica substrate. The polariser 20 consists of a pair of polariser plates 34 each including a wire array or grid 30. The polariser plates 34 are mounted facing one another with an air gap 36 between them and such that the wire arrays 30 are positioned in parallel.

Such a pair of wire grid polariser plates can yield a contrast in excess of 500 at 255 nm. This contrast is greatly superior to that of a single polarising filter.

The custom wire grid polariser 20 delivers a number of advantages resulting in a more compact apparatus. In particular, the wire grid polariser 20 is significantly thinner than polarisers used in similar apparatus, having a thickness of only around 2.2 mm. Each polariser plate 34 has a thickness of around 1 mm+/−0.1 mm and a 0.2 mm air gap 36 between the polariser plates. As a result the polariser 20 takes up much less space than conventional high contrast polarisers. Furthermore, the custom polariser 20 has no requirement for collimation of the incident beam of light and no restrictions on the angle of incidence.

Use of the custom wire grid polariser 20 provides the apparatus or apparatus accessory as the case may be, with a ten fold increase in the speed of each measurement. Moreover, it provides measurements of reflected light having wavelengths down to 250 nm, which conventional high contrast polarisers cannot do without restricting the angles of incidence whilst maintaining good polarisation contrast.

The detector assembly 14 comprises an infra red transmitting detector in combination with an infra red detector. The infra red detector is a photovoltaic detector. Photovoltaic detectors made from materials such as silicon (Si), germanium (Ge), or indium gallium arsenide (InGaAs) are sufficiently uniform by virtue of their manufacturing process, making them suitable for direct collection of a beam of light. A silicon detector covers a wavelength range from less than 200 nm to approximately 1100 nm. An InGaAs detector cover various ranges depending on the ratio of indium to gallium used to form the detector, ranging from 800 nm to a long wavelength limit between 1,700 nm and 2,500 nm.

As a result for applications involving measurement of specular reflectance of materials intended to withstand solar radiation or for solar power applications, in order to cover a sufficient wavelength range, i.e. wavelengths ranging from 250 nm to 2,500 nm, it is generally necessary to employ multiple detectors. This substantially increases the complexity of the apparatus since means for switching between the detectors must be provided in the form of a mechanical movement of each detector, or a mechanical movement of an optical component to shift the beam of light. These types of mechanisms invariably add bulk and complexity to the apparatus.

Accordingly, a custom detector assembly 14 has been developed that effectively combines two detectors in an encapsulation, thereby enabling a broad spectrum of wavelengths to be covered without requiring a mechanical shift in the detectors or the beam of light. Within the encapsulation, a first silicon detector is mounted on a second infra red detector. In operation, light having wavelengths from approximately 200 nm to 1,100 nm is absorbed by the silicon detector to produce an electrical signal. For light having wavelengths above 1,100 nm, the first silicon detector becomes transparent and the beam of light passes through to the second detector beyond, which absorbs the beam of light to produce its electrical signal.

The detector assembly 14 consists of a 5 mm square silicon detector mounted over a 3 mm diameter InGaAs detector. The two detectors are encapsulated together with a Peltier cooler and a thermistor to cool and stabilise the detectors. This custom detector assembly 14 provides capacity for an accessory apparatus design that is simple and compact and whilst maintaining uniform detectors.

Alternative detector assemblies exhibiting similar properties to the preferred arrangement include germanium indium gallium arsenide (Ge/InGaAs) detectors.

Whilst combinations that include lead sulphide detectors (PbS), such as silicon lead sulphide (Si/PbS) detectors exhibit similar crossover properties, they are not deemed to be suitable for this application since the lead sulphide detectors use a manufacturing process that does not yield a detector having a sufficiently uniform response across its surface.

Referring now to FIG. 2, the detector assembly 14 may include an optical component such as a mirror or lens 24 to focus the beam of light which is specularly reflected from the surface of the sample 22 onto the detector assembly. Preferably, the reflected beam of light is focussed onto the indium gallium arsenide (InGaAs) detector over which the silicon detector is mounted, to form a reduced image of the reflected beam thereon. A lens or mirror may be used for this purpose. A toroid or an ellipsoid mirror has been found to be particularly suitable for this application.

Focussing the reflected beam of light on the detector assembly in this way allows a smaller detector to be used and smaller detectors offer an enhanced signal to noise ratio. Using an optical component to refocus the reflected beam of light thereby reduces the sensitivity of the apparatus to misalignment of the angle of rotation of the detector assembly 14 and also to the condition of the surface of the sample 22.

Where the terms "comprise", "comprises" "Comprised" or "comprising" are used in this specification (including the claims), they are to be interpreted as specifying the presence of stated features, integers, steps or components referred to, but not preclude the presence of one or more other feature, integer, step, component or group thereof.

While the invention has been described in conjunction with a limited number of embodiments, it will be appreciated by those skilled in the art that many alternative, modifications and variations in light of the foregoing description are possible. Accordingly, the present invention is intended to embrace all such alternative, modifications and variations as may fall within the spirit and scope of the invention as disclosed.

What is claimed is:

1. An accessory apparatus for a spectrometer for measuring specular reflectance of a sample, the apparatus comprising:
    a polarizing filter comprising a wire grid so as to avoid a need for collimation of an incident beam of light emitted by a light source, wherein the beam of light is transmitted onto a surface of the sample at an angle of incidence; and
    a detector assembly for detecting a beam of light which is specularly reflected from the surface of the sample,
    wherein the polarizing filter comprises a pair of polarizer plates, each polarizer plate including a wire array, the polarizer plates being mounted face to face with an air gap there between, such that the wire arrays are in parallel.

2. The accessory apparatus according to claim 1, wherein the polarizing filter provides a contrast of greater than 500 at 255 nm.

3. The accessory apparatus according to claim 1, wherein the polarizing filter has a thickness of about 2 mm to about 5 mm.

4. The accessory apparatus according to claim 1, wherein the polarizing filter has a thickness of 2.2 mm.

5. The accessory apparatus according to claim 1, wherein the detector assembly comprises an infra red transmitting detector and an infra red detector.

6. The accessory apparatus according to claim 5, wherein the infra red detector is a photovoltaic detector.

7. The accessory apparatus according to claim 6, wherein the photovoltaic detector comprises an indium gallium arsenide (InGaAs) detector.

8. The accessory apparatus according to claim 1, wherein the detector assembly comprises a silicon detector mounted above an indium gallium arsenide (InGaAs) detector.

9. The accessory apparatus according to claim 8, wherein the silicon detector is approximately 5 mm square.

10. The accessory apparatus according to claim 9, wherein the indium gallium arsenide (InGaAs) detector is approximately 3 mm in diameter.

11. The accessory apparatus according to claim 1, further comprising:
    an optical component for focusing the beam of light which is specularly reflected from the surface of the sample onto the detector assembly.

12. The accessory apparatus according to claim 11, wherein the beam of light which is specularly reflected from the surface of the sample is focused onto an indium gallium arsenide (InGaAs) detector.

13. The accessory apparatus according to claim 11, wherein the optical component comprises a toroid mirror.

14. The accessory apparatus according to claim 11, wherein the optical component comprises an ellipsoid mirror.

15. The apparatus according to claim 1, wherein the light source, the detector and the sample holder are correspondingly relatively positionable for a specularly reflected component of a transmitted light beam to be detected for different angles of incidence of the light beam and wherein corresponding relative positions of the light source, the sample surface and the detector are constrained such that said detector is located by said constraint to detect said specularly reflected component of said light beam at an angle of reflection, which is equal to the angle of incidence of the light beam on the sample surface, and wherein the detector for movement along an arc about said axis and the sample holder and the detector are operatively associated such that movement of the sample holder through an angle automatically rotates the detector through twice said angle.

16. The apparatus according to claim 1, further comprising:
- a spectrometer, positioned between the light source and the polarizing filter, for selecting a limited bandwidth of the beam of light for presentation to the surface of the sample.

* * * * *

UNITED STATES PATENT AND TRADEMARK OFFICE
CERTIFICATE OF CORRECTION

PATENT NO. : 8,531,673 B2
APPLICATION NO. : 13/165376
DATED : September 10, 2013
INVENTOR(S) : Robert John Francis It is certified that error appears in the above-identified patent and that said Letters Patent is hereby corrected as shown below:

In the Specification

In column 1, line 3, Below "Title" insert -- CROSS REFERENCES TO RELATED APPLICATIONS
This application claims the benefit of Australian Patent Application No. 2010903271 filed on July 21, 2010, the subject matter of which is hereby incorporated by reference. --.

Signed and Sealed this
Nineteenth Day of November, 2013

Teresa Stanek Rea
*Deputy Director of the United States Patent and Trademark Office*